(12) United States Patent
Kronmueller et al.

(10) Patent No.: US 10,857,367 B2
(45) Date of Patent: Dec. 8, 2020

(54) FEEDTHROUGH OF AN IMPLANTABLE MEDICAL ELECTRONIC DEVICE

(71) Applicant: BIOTRONIK SE & CO. KG, Berlin (DE)

(72) Inventors: Daniel Kronmueller, Nuremberg (DE); Michael Arnold, Erlangen (DE)

(73) Assignee: BIOTRONIK SE & Co. KG, Berlin (DE)

( * ) Notice: Subject to any disclaimer, the term of this patent is extended or adjusted under 35 U.S.C. 154(b) by 325 days.

(21) Appl. No.: 15/824,473

(22) Filed: Nov. 28, 2017

(65) Prior Publication Data

US 2018/0161582 A1   Jun. 14, 2018

(30) Foreign Application Priority Data

Dec. 9, 2016   (EP) .................................. 16203193

(51) Int. Cl.
| | |
|---|---|
| *A61N 1/37* | (2006.01) |
| *A61N 1/375* | (2006.01) |
| *A61N 1/05* | (2006.01) |
| *H01B 17/30* | (2006.01) |

(52) U.S. Cl.
CPC ......... *A61N 1/3754* (2013.01); *A61N 1/0541* (2013.01); *H01B 17/303* (2013.01)

(58) Field of Classification Search
CPC ... A61N 1/3754; A61N 1/0541; H01B 17/303
See application file for complete search history.

(56) References Cited

U.S. PATENT DOCUMENTS

| | | | |
|---|---|---|---|
| 7,747,321 B2 | 6/2010 | Fischbach et al. | |
| 8,536,468 B2 | 9/2013 | Teske | |
| 9,065,224 B2 | 6/2015 | Marzano et al. | |
| 9,692,173 B2 | 7/2017 | Marzano et al. | |
| 2007/0179553 A1* | 8/2007 | Iyer ...................... | A61N 1/3754 607/37 |
| 2007/0239222 A1 | 10/2007 | Sprain et al. | |
| 2008/0119906 A1 | 5/2008 | Starke | |
| 2009/0079519 A1 | 3/2009 | Iyer | |
| 2011/0203841 A1* | 8/2011 | Gradtke ................. | H01R 12/58 174/261 |

(Continued)

FOREIGN PATENT DOCUMENTS

| | | |
|---|---|---|
| EP | 2371418 A2 | 10/2011 |
| EP | 2529790 A1 | 12/2012 |

*Primary Examiner* — Amanda K Hulbert
*Assistant Examiner* — Natasha Patel
(74) *Attorney, Agent, or Firm* — Laurence A. Greenberg; Werner H. Stemer; Ralph E. Locher

(57) ABSTRACT

A feedthrough for an implantable medical electronic device that has a housing and a header. The feedthrough having an insulator that has a housing-side surface and a header-side surface opposite it, a feedthrough flange surrounding the insulator, and at least one primary connection element penetrating the insulator and for connection of an electrical or electronic component of the device. This electrical or electronic component is arranged in the housing. The connection element is fastened by a hard solder connection, so that it is fluid-tight in a passage of the insulator. The primary connection element has a housing-side end that is essentially even with the housing-side surface of the insulator or is recessed into the insulator with respect to this surface.

19 Claims, 4 Drawing Sheets

(56) References Cited

U.S. PATENT DOCUMENTS

| | | | |
|---|---|---|---|
| 2013/0338750 A1* | 12/2013 | Eck | A61N 1/362 |
| | | | 607/119 |
| 2014/0262493 A1 | 9/2014 | Markham et al. | |
| 2014/0272457 A1 | 9/2014 | Watada | |
| 2016/0001387 A1 | 1/2016 | Kronmueller et al. | |
| 2017/0294250 A1* | 10/2017 | Giese | H01B 19/00 |

* cited by examiner

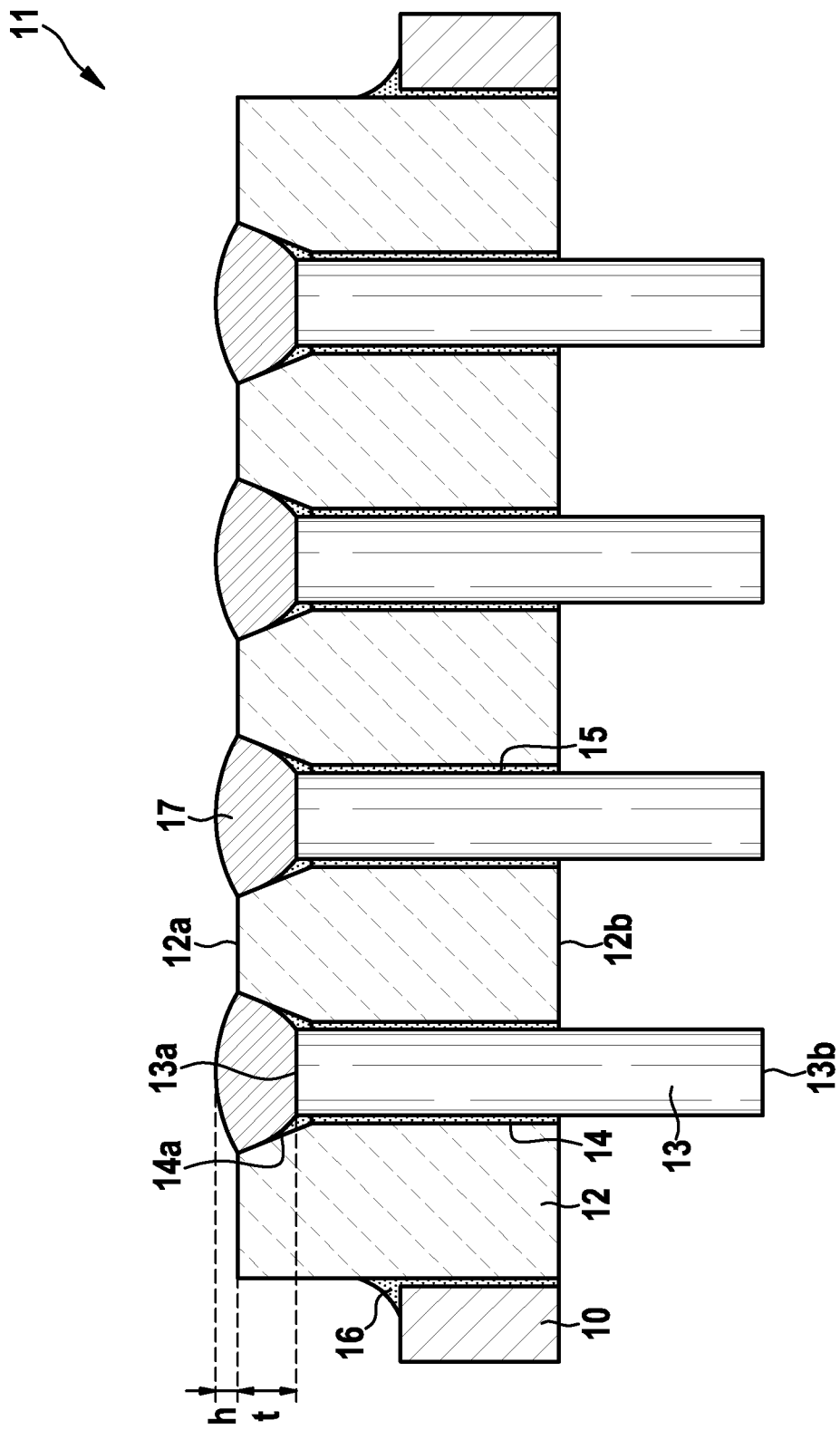

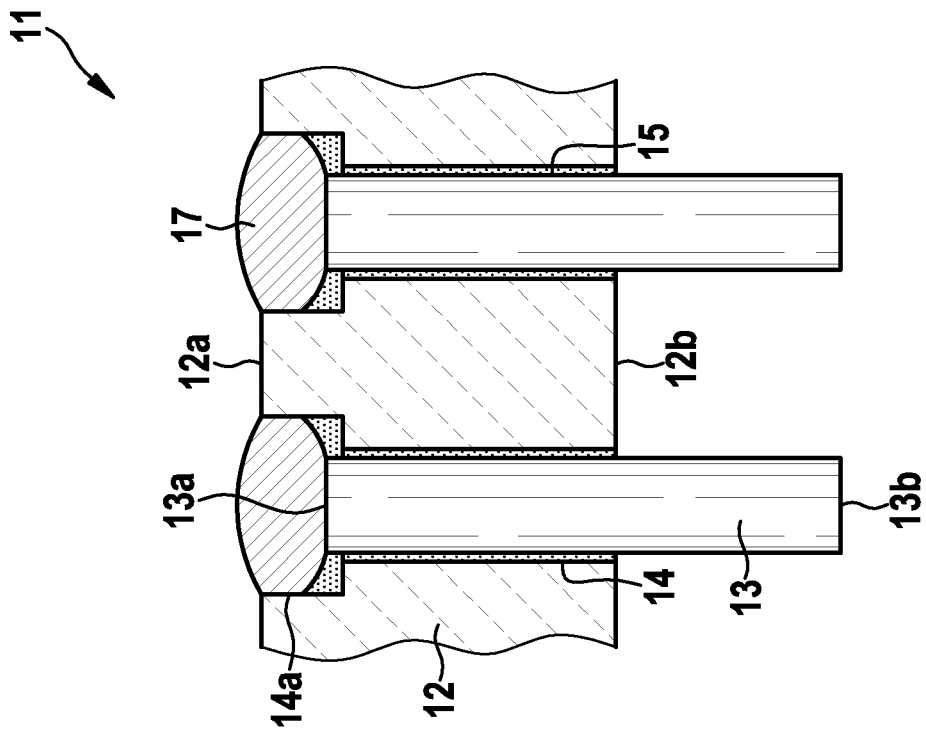
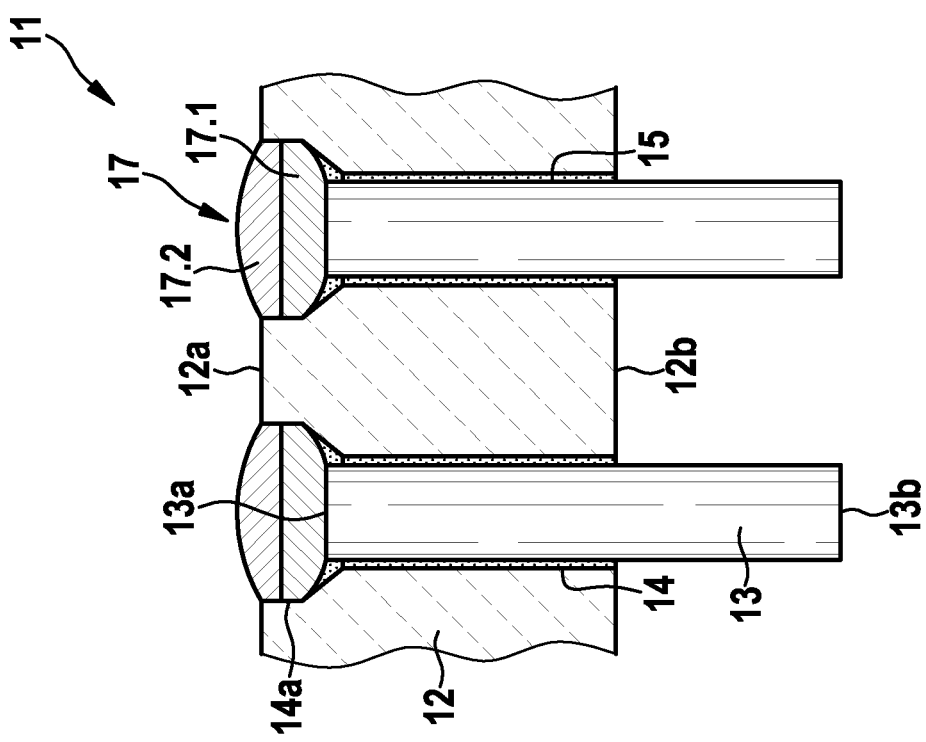

FEEDTHROUGH OF AN IMPLANTABLE MEDICAL ELECTRONIC DEVICE

CROSS-REFERENCE TO RELATED APPLICATION

This application claims the benefit, under 35 U.S.C. § 119, of European patent application EP 16203193.4, filed Dec. 9, 2016; the prior application is herewith incorporated by reference in its entirety.

BACKGROUND OF THE INVENTION

Field of the Invention

The invention relates to a feedthrough of an implantable medical electronic device.

Such feedthroughs are especially suitable for electromedical implants, such as implantable cardiac pacemakers, defibrillators, cardioverters, nerve and brain stimulators, hearing aids, implantable drug pumps, or other electrically active implants that contain a hermetically sealed housing, and batteries with a hermetically sealed housing for these electronic implants. Furthermore, the invention relates to an implantable medical electronic device with such a feedthrough.

Most implantable electromedical devices (IMDs) of practical importance are provided to deliver, through suitably placed electrodes, electrical pulses to excitable body tissue. Furthermore, many devices can selectively measure electrical pulses and stimuli in the body of the patient and record or assess them over a longer period of time to select an individually adapted therapy and to check the success of the treatment in vivo.

To execute these functions, the device has, inside the housing, electronic/electrical functional units for producing and measuring the pulses and for suitable control of the production of pulses, and the device has, on the outside, electrodes directly on it or connections for at least one electrode lead, the distal end section of these connections containing the electrodes for transferring pulses to the tissue. The electronic/electrical functional units inside the device are to be connected with the outside electrodes or electrode lead connections in a way that ensures absolutely and permanently reliable function under the special conditions of the implanted state.

The task of a feedthrough is to carry the electrical signals through the hermetically sealed housing and in this way to allow the electronics in the hermetically sealed housing to make electrical contact with the electrodes in the body of the patient. To accomplish this, the feedthrough has an interface on the body side and an interface on the electronics side for connecting the electrical signals. In many such feedthroughs, this is done using connection pins that make contact with the printed circuit board or with a similar conductor support located inside the device, and carry the signals through the housing, ending in a header especially in many IMDs.

Usually, the feedthroughs of the electromedical devices (IMDs) have a flange with which they are inserted in a housing wall of the electromedical implant, preferably through a thermal joining process such as welding, hard soldering (brazing), or soft soldering. The housing contains an electronic apparatus, normally with a circuit board, among other things, that is able to process or send electrical signals.

The feedthrough typically has at least one feedthrough sleeve and a flange surrounding the at least one feedthrough sleeve, which has at least one connection pin sitting in it that is surrounded by the feedthrough sleeve. The connection pin extends through the flange and the feedthrough sleeve from an inner end inside the housing to an outer end, which lies outside the hermetically sealed housing.

As a rule, the connection pin is connected with the feedthrough sleeve and/or the feedthrough sleeve is connected with the flange by a solder connection, preferably using a gold solder if the feedthrough sleeve has metal coating (for example a niobium coating), or using a biocompatible solder glass (type 8625 of the Schott company) if uncoated feedthrough sleeves are used.

In view of the fact that in the case of a medical implant the external end of the connection electrode can come in contact with the body tissue surrounding the implant, the connection pins are, as a rule, made of a biocompatible material, such as, for example, niobium (Nb), platinum (Pt), iridium (Ir), platinum/iridium alloys (Pt/Ir), tantalum (Ta), titanium (Ti), zirconium (Zr), hafnium (Hf), medical stainless steel (e.g., 316L) or alloys made of these materials. Materials that are also possible for the connection pin are Fe—Ni, FeNiCo, FeCr, molybdenum (Mo), tungsten (W), chromium (Cr), FeCr, vanadium (V), aluminum (Al), or other alloys of these materials.

U.S. Pat. No. 7,747,321 B2 discloses a cardiac pacemaker 1, as shown in FIG. 1, with a pacemaker housing 3 and a header 5, which has a printed circuit board (PCB) 7 arranged inside it, along with other electronic components, and whose lead connector (not shown) arranged in the header is connected with an electrode lead 9. A feedthrough 11 provided between the device housing 3 and the header 5 contains multiple connection pins 13. On the housing-side end, the connection pins are inserted through corresponding holes in the printed circuit board and soft-soldered with it. They comprise a wire core, made, for instance, of tantalum, niobium, titanium, molybdenum, copper, and an oxidation resistant sheath made of a biocompatible material, for instance gold, platinum, titanium, or something similar.

The connection pins are typically connected with the conductor support arranged in the housing by welding, bonding, crimping, soft soldering, or cementing. In recent years, especially soft soldering (reflow soldering) has strongly gained in importance, since it is a very economical process. The materials usually used for the connection pins are poorly suited for this connection process, so that various strategies have been developed for further processing of the feedthrough to connect it to the conductor support using a sufficiently controllable process with justifiable costs. Corresponding approaches are disclosed in published, European patent application EP 2 371 418 A1 (corresponding to U.S. Pat. No. 8,536,468) or U.S. patent publication No. 2016/0001387 A1 of the applicant, or also in published, European patent application EP 2 529 790 A1 (corresponding to U.S. Pat. Nos. 9,065,224 and 9,692,173), among other places.

The connection pins are typically connected with the electrodes or the plugs for the electrodes in the header by welding. Other joining processes such as, e.g., soft soldering, hard soldering, bonding, cementing, and crimping are also possible, however are rarely used in practice.

During the course of miniaturization and the progress in electronics, there has been has rapid change in the soft soldering technique in recent years. Manual assembly processes have been increasingly displaced by fully automatic pick & place machines, and through hole technology (THT) has been gradually replaced by surface mount technology (SMT). This allows smaller, more compact circuits, and thus has also gradually led to smaller, more patient-friendly IMDs. In order to be able to achieve the many advantages of the SMT, feedthroughs must satisfy the requirements on a surface-mount device (SMD).

The overall assembly processes for feedthroughs of the type mentioned have shown certain problems, especially when SMT is used, such as above all considerable susceptibility of the feedthroughs, especially the connection pins, to deformation and damage. To prevent this, special measures are taken to protect the ends of the connection pins, and suitable test procedures are carried out to ensure that a dimensionally accurate and reliable electrical contact can be made with the conductor support. Both types of measures take a lot of effort and make the further processing of the known feedthroughs relatively costly.

SUMMARY OF THE INVENTION

The invention has the goal of indicating a hermetically sealed feedthrough for implants, this feedthrough being made of a biocompatible material toward the outside of the implant and being connectable by a simple production technique to make contact with the electronics arranged at its inside end, especially by means of reflow soldering.

This is accomplished by a feedthrough having the features of the main claim. Expedient further developments of the inventive idea are the subject of the dependent claims.

The invention includes the idea of fundamentally departing from the previous approach that involves precautions and testing measures for the connection pins protruding from the feedthroughs, and instead eliminating the potential error source from the start. Accordingly, the or every primary connection element has at least one end that is essentially level with the surface of the insulator or recessed into the insulator with respect to this surface. This completely eliminates the susceptibility of the known feedthroughs to deformations and damage of the ends of the connection pins, and makes it possible to eliminate elaborate precautions and test procedures.

According to a relatively independent aspect of the invention, at the end of the primary connection element, or every primary connection element, the corresponding passage has a widening, which serves as a material reservoir. Depending on the specific connection technology used to connection the connection pins with the insulator, on the one hand, and the connection pins with the conductor support, on the other hand, the material reservoir is at least partly filled with suitable materials or material combinations or layers, and facilitates the precise feed of material for the respective process steps.

In expedient embodiments, the widening is cylindrical, frustum-shaped, or bowl-shaped. In principle other shapes of the widening are also possible, however, the ones mentioned here are the most expedient from the current technological perspective.

In one embodiment of the invention, the widening of the passage is partly filled with a hard solder, which simultaneously surrounds the connection element in the passage, and the surface of the hard solder and optionally of the housing-side end face of the connection element has a soft solder or sintered material on it. In one embodiment, the widening has a first, non-soft solderable sintered material and a second soft solderable sintered material in it along with the hard solder. In another embodiment, the widening has a first, higher melting hard solder in it, and a second, lower melting hard solder on its surface.

In other embodiments of the invention, the housing-side end of the connection element or every connection element is recessed into the housing-side surface of the insulator, and covered with a hard solder or sintered material or soft solder layer. This cover is configured so that the covering material layer has a surface that is even with the housing-side surface of the insulator or bulges out of the housing-side surface of the insulator. In practically realized embodiments, the maximum height of a patelliform or meniscus-shaped covering material layer with respect to the housing-side surface of the insulator is in the range between 0.01 and 1 mm, depending on the size of the feedthrough.

In another embodiment of the invention, the secondary connection element is electrically conductively joined with the primary connection element and the secondary connection element has at least one soft solderable point of contact. Here the secondary connection element or every secondary connection element is connected with the corresponding primary connection element through a soft solder, a low-melting hard solder, or a sintered material, or it consists of a soft solder, a low-melting hard solder, or a sintered material.

In practically relevant embodiments, the secondary connection element, or at least one secondary connection element, is spherical, elliptical, or polyhedral. It is also possible for the various geometric configurations of individual secondary contact elements in one and the same feedthrough to be different, in order to take optimal account of, for instance, special conductor configurations on the conductor support to be connected to the feedthrough.

To facilitate process control in the following steps, other embodiments provide that at least one surface of the secondary connection element, or of every secondary connection element protruding out of the housing-side surface of the insulator be coated with a material improving the soft-solderability or sinterability, in particular Cu, Ni, Ag, Sn, Au, Pt, Ir, Pd, or alloys of at least two of these or a layer system improving the soft-solderability, such as, EPIG, ENEPIG, HAL, or something of that kind. It goes without saying that the specific coating system is selected and optimized according to the specifics of the following process for connecting the feedthrough.

Other features which are considered as characteristic for the invention are set forth in the appended claims.

Although the invention is illustrated and described herein as embodied in a feedthrough of an implantable medical electronic device, it is nevertheless not intended to be limited to the details shown, since various modifications and structural changes may be made therein without departing from the spirit of the invention and within the scope and range of equivalents of the claims.

The construction and method of operation of the invention, however, together with additional objects and advantages thereof will be best understood from the following description of specific embodiments when read in connection with the accompanying drawings.

BRIEF DESCRIPTION OF THE SEVERAL VIEWS OF THE DRAWING

FIG. 2 is a diagrammatic, longitudinal sectional representation of a sample embodiment of a feedthrough according to the invention;

FIG. 3 is a longitudinal sectional representation of another embodiment of the inventive feedthrough; and FIG. 4 is a longitudinal sectional representation of another embodiment of the inventive feedthrough.

DETAILED DESCRIPTION OF THE INVENTION

Figure 1:
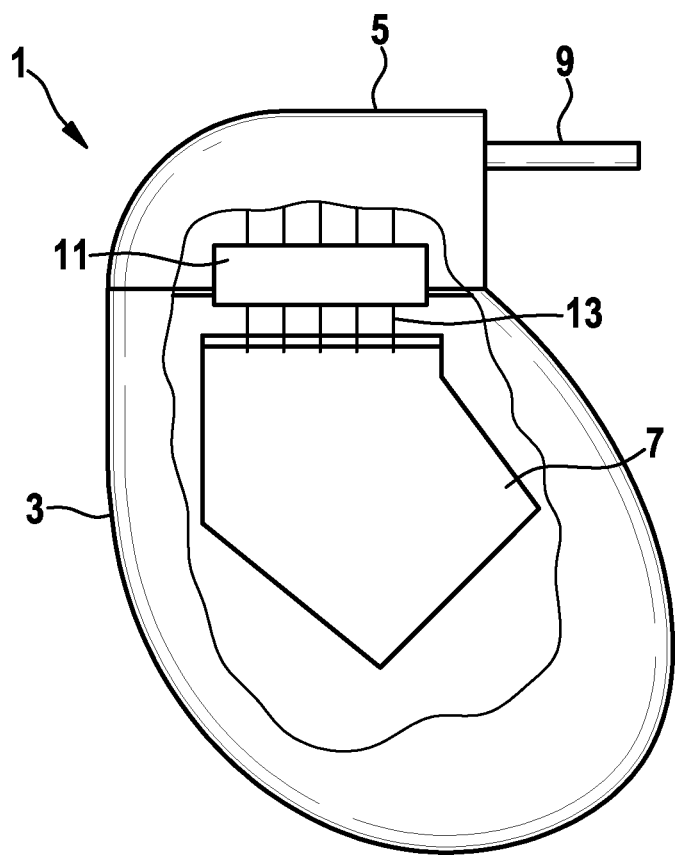
FIG. 1 is a schematic representation of a conventional cardiac pacemaker.

Referring now to the figures of the drawings in detail and first, particularly to FIGS. 2-5 thereof, there is shown a feedthrough being uniformly designated with number 11 as in FIG. 1, independent of the differing geometric shapes and arrangements of their parts and details, and the designation of the individual sections or the respective coating is correspondingly selected.

FIG. 2 shows a feedthrough 11 with an insulator 12 made of insulating ceramics, the insulator 11 being surrounded by a feedthrough flange 10 and being inserted with multiple connection pins 13. The connections between the connection pins 13 and the walls of the insulator's passages or holes 14 holding them, and the connections between the outer periphery of the insulator 12 and the inner periphery of the feedthrough flange 10 are each formed by a hard solder element 15 or 16.

The basically cylindrical holes 14 in the insulator 12 are provided with conical widening sections 14a on a first surface 12a of the insulator, this surface being the housing-side surface in the state in which it is used. The connection pins 13 are recessed with respect to the housing-side surface 12a of the insulator 12, while the opposite ends 13b of the connection pins project out of the opposite (header-side) surface 12b of the insulator.

The recessed housing-side ends 13a of the connection pins 13 have a plug 17 made of soft solderable solder material or sintered material applied above them, the plug filling the conical widening section 14a of each associated hole above a hard solder 15. The plug 17 extends to a depth of t from the housing-side surface 12a into the hole 14, and bulges up out of the surface 12a in the shape of a cupola with a maximum height of h. It serves as a contact area for later soldering of the feedthrough with a printed circuit board or a similar element of the electronics in the device housing of an IMD, this printed circuit board or similar element of the electronics being arranged on the housing side.

FIG. 3 schematically shows another smaller feedthrough 11, but can also be understood as a representation of a section of a larger feedthrough that contains more than the two connection pins 13 shown in FIG. 3. A feedthrough flange is not shown here, but can be present. The configuration of the hole 14 holding the connection pins and the positioning of the connection pins 13 is similar to that in the feedthrough according to FIG. 2, with the now described differences.

The shape of the widening sections 14a on the housing-side surface 12a of the insulator 12 is not conical here, but rather the widening sections comprise a lower conical section and an upper cylindrical section. Furthermore, in these widening sections and on the housing-side end face 13a of the connection pins 13 there is a two-part material plug 17 that contains a lower layer 17.1 that lies on the connection pin end face 13a and that is made of a non-soft solderable solder or sintered material, and a layer 17.2 on it that covers the lower layer and that is made of a soft solderable solder or sintered material.

Putting the (second) hard solder or sintered material, which has a lower melting point than the hard solder of the hard solder elements 15, into the widening section in the layer 17.1 makes it possible to compensate for differences in the level of the holes 14 that can result from the process in the individual process steps of manufacturing the feedthrough, and this compensation for differences in the level of the holes 14 in turn makes it possible to avoid undesired deviations in the electrical properties of the feedthrough in the individual areas of the connection. The material is connected by hard soldering or sintering to the hard solder elements 15 in the annular gap between inner wall of the hole 14 and the outer wall of the connection pin 13.

FIG. 4 shows another variation of the feedthrough 11 with a structure that is once again similar to that of the feedthroughs according to FIGS. 2 and 3. However, here the widening sections 14a of the openings or holes 14 holding the connection pins 13 are in the form of stepped cylindrical widenings, and part of the widening is filled with remaining material of the hard solder elements 15 and another part (in the upper area) is filled with a soft solder plug 17.

Figure 5:
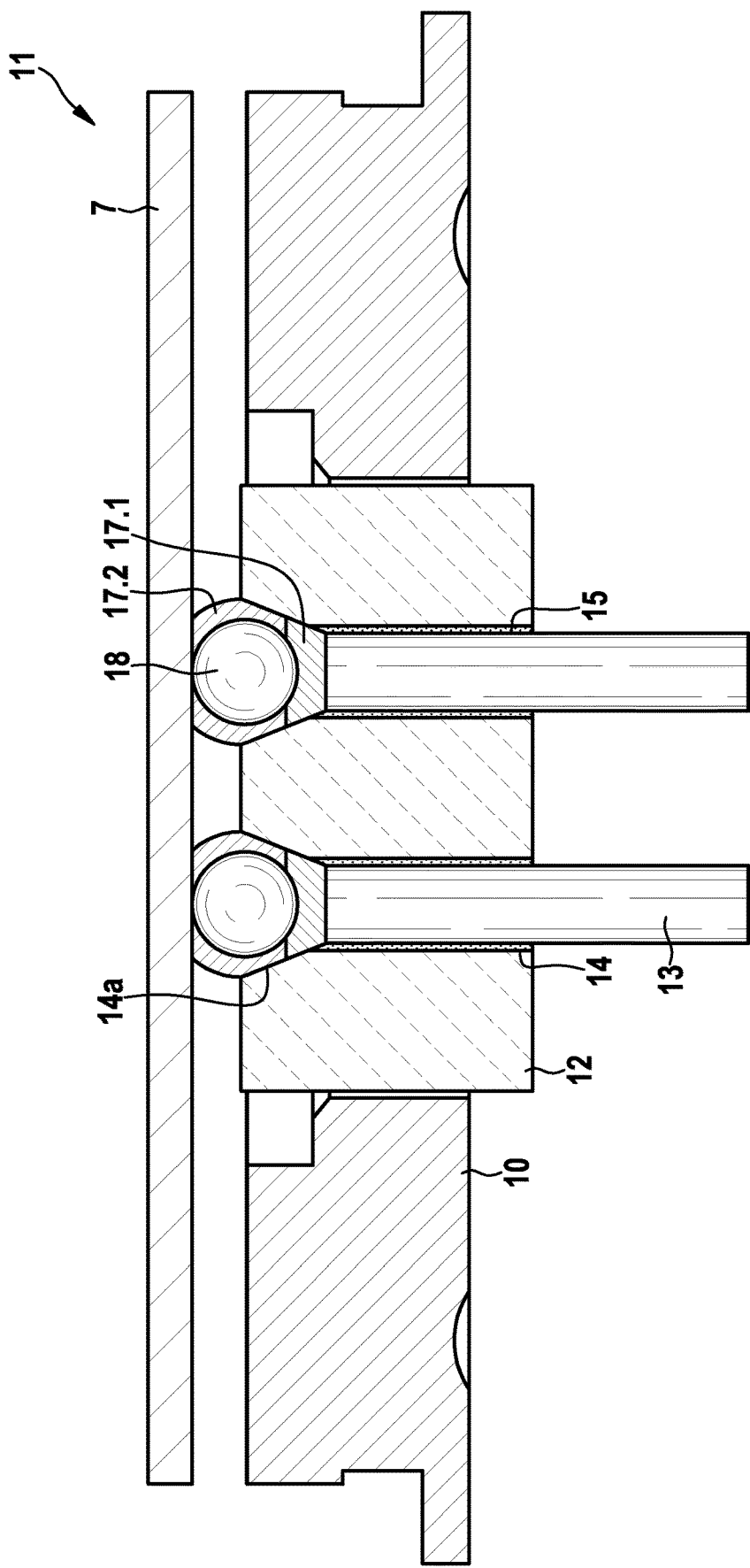
FIG. 5 is a schematic cross sectional representation of another inventive feedthrough.

FIG. 5 shows a schematic cross sectional representation of another feedthrough 11 associated with a printed circuit board 7, on which it is mounted. The basic structure of the feedthrough 11 once again corresponds to the embodiments according to FIGS. 2 through 4, including the widening sections 14a of the holes 14 for the connection pins 13.

However here the widening sections 14a have not only a first non-soft solderable solder or sintered material 17.1 and a second soft solderable solder or sintered material 17.2 put into them, but rather a metal ball 18 is additionally provided as a secondary connection element, along with the connection pin 13, which in this context should be designated as the primary connection element. This structure makes it especially simple to connect the feedthrough with corresponding conductor tracks on the printed circuit board 7 using the technique of reflow soldering.

After the hard soldering, the holes 14 are filled with the lower-melting hard solder, soft solder, or a sintered paste 17.1. Filling a pasty compensating mass into the holes compensates for differences in level due to the different melting behavior of the hard solder in the ceramic.

The polyhedral, oval, or round secondary connection element 18 is set onto the pasty, low-melting hard solder, soft solder, or sintered paste 17.1. These elements 18 consist, e.g., of easily available materials (e.g., tungsten carbide, 1.4125). The surface of the element 18 is finished by the galvanic process, giving it very good soft solderability or sinterability. This can be achieved by coating it with Ni and Ag or Ni and Sn. Furthermore, it is possible to use surface coating systems known from the literature (e.g., EPIG, ENEPIG, HAL), which achieve permanent solderability.

The automated assembly of the secondary connection elements is very simple, since their geometry makes them very simple to isolate and feed. Elements lost during assembly roll off automatically, and thus do not need to be removed manually or by means of visual inspection of the product.

Joining the connection elements creates a soft solderable and surface-mountable electrical feedthrough for medical purposes. The simple assembly allows both manual and automated manufacturing to be very economical.

Many other variants of the embodiments of the invention shown here in the examples and aspects of the invention emphasized further above are possible.

It will be apparent to those skilled in the art that numerous modifications and variations of the described examples and embodiments are possible in light of the above teaching. The disclosed examples and embodiments are presented for purposes of illustration only. Other alternate embodiments may include some or all of the features disclosed herein. Therefore, it is the intent to cover all such modifications and alternate embodiments as may come within the true scope of this invention.

The invention claimed is:

1. An electrical feedthrough of an implantable medical electronic device having a housing and a header, the electrical feedthrough comprising:
an insulator having a first housing-side surface and a second surface opposite said first housing-side surface, said second surface facing away from the housing, said insulator having at least one passage formed therein;
a feedthrough flange surrounding said insulator;
a hard solder connection; and
at least one primary connection element penetrating said insulator, for forming a connection to an electrical or electronic component of the implantable medical electronic device, the electrical or electronic component being disposed in the housing, said primary connection element being fastened, by means of said hard solder connection, so that said primary connection element is fluid-tight in said passage through said insulator, said primary connection element having a housing-side end, wherein said housing-side end of said primary connection element being recessed into said first housing-side surface of said insulator, and covered with a hard solder or sintered material or soft solder layer so that a covering material layer has a surface that is even with said first housing-side surface of said insulator or forms a cupola bulging up out of said first housing-side surface of said insulator.

2. The electrical feedthrough according to claim 1, wherein:
said second surface is a header-side surface; and
said at least one primary connection element is one of a plurality of primary connection elements.

3. The feedthrough according to claim 1, wherein said cupola of said covering material layer has a maximum height with respect to said first housing-side surface of said insulator in a range between 0.01 and 1 mm.

4. The feedthrough according to claim 1, further comprising a secondary connection element electrically conductively joined with said primary connection element and said secondary connection element has at least one soft solderable point of contact.

5. The feedthrough according to claim 4, wherein said secondary connection element is connected with said primary connection element through a soft solder, a low-melting hard solder, or a sintered material, or said secondary connection element consists of said soft solder, said low-melting hard solder, or said sintered material.

6. The feedthrough according to claim 4, wherein said secondary connection element is spherical shaped, elliptical shaped, or polyhedral shaped.

7. The feedthrough according claim 4, wherein at least one surface of said secondary connection element protruding out of said first housing-side surface of said insulator is coated with a material improving a soft-solderability or sinterability and selected from the group consisting of Cu, Ni, Ag, Sn, Au, Pt, Ir, Pd, and alloys of at least two of these or a layer system improving the soft-solderability selected from the group consisting of EPIG, ENEPIG and HAL.

8. A feedthrough of an implantable medical electronic device having a housing and a header, the feedthrough comprising:
an insulator having a first housing-side surface and a second surface opposite said first housing-side surface, said second surface facing away from the housing, said insulator having a least one passage with a widening section formed therein;
a feedthrough flange surrounding said insulator;
a hard solder connection; and
at least one primary connection element penetrating said insulator, for connection to an electrical or electronic component of the implantable medical electronic device, the electrical or electronic component being disposed in the housing, said primary connection element being fastened, by said hard solder connection, so that said primary connection element is fluid-tight in said passage of said insulator, said primary connection element having a housing-side end extending into said widening section of said passage serving as a material reservoir, wherein said housing-side end of said primary connection element being recessed into said first housing-side surface of said insulator, and covered with a hard solder or sintered material or soft solder layer so that a covering material layer has a surface that is even with said first housing-side surface of said insulator or forms a cupola bulging up out of said first housing-side surface of said insulator.

9. The feedthrough according to claim 8, wherein said widening section is cylindrical-shaped, frustum-shaped, or bowl-shaped.

10. The feedthrough according to claim 8, wherein said widening section of said passage is partly filled with a hard solder, which simultaneously surrounds said primary connection element in said passage, and a surface of said hard solder and of said housing-side end of said primary connection element has a soft solder or soft solderable sintered material on it.

11. The feedthrough according to claim 10, further comprising a first, non-soft solderable sintered material and a second soft solderable sintered material disposed in said widening section along with said hard solder.

12. The feedthrough according to claim 10, further comprising:
a first, higher-melting hard solder disposed in said widening section; and
a second lower-melting hard solder disposed on a surface of said widening section.

13. The feedthrough according to claim 8, wherein said cupola of said covering material layer has a maximum height with respect to said first housing-side surface of said insulator in a range between 0.01 and 1 mm.

14. The feedthrough according to claim 8, further comprising a secondary connection element electrically conductively joined with said primary connection element and said secondary connection element has at least one soft solderable point of contact.

15. The feedthrough according to claim 14, wherein said secondary connection element is connected with said primary connection element through a soft solder, a low-melting hard solder, or a sintered material, or said secondary connection element consists of said soft solder, said low-melting hard solder, or said sintered material.

16. The feedthrough according to claim 14, wherein said secondary connection element is spherical shaped, elliptical shaped, or polyhedral shaped.

17. The feedthrough according claim 14, wherein at least one surface of said secondary connection element protruding out of said first housing-side surface of said insulator is coated with a material improving a soft-solderability or sinterability and selected from the group consisting of Cu, Ni, Ag, Sn, Au, Pt, Ir, Pd, and alloys of at least two of these or a layer system improving the soft-solderability selected from the group consisting of EPIG, ENEPIG and HAL.

18. The electrical feedthrough according to claim 8, wherein:
said second surface is a header-side surface; and
said at least one primary connection element is one of a plurality of primary connection elements.

19. An implantable medical electronic device selected from the group consisting of a cardiac pacemaker, an implantable cardioverter and a cochlear implant, the implantable medical electronic device comprising:
a feedthrough according to claim 1.

* * * * *